United States Patent [19]

Goudie

[11] 4,382,959
[45] May 10, 1983

[54] NAPHTHALENE DERIVATIVES, A PROCESS FOR THEIR PREPARATION AND THEIR USE IN ANTI-INFLAMMATORY PHARMACEUTICAL COMPOSITIONS

[75] Inventor: Alexander C. Goudie, Harlow, England

[73] Assignee: Beecham Group Limited, England

[21] Appl. No.: 253,197

[22] Filed: Apr. 13, 1981

Related U.S. Application Data

[63] Continuation of Ser. No. 94,101, Nov. 14, 1979, abandoned.

[30] Foreign Application Priority Data

Nov. 23, 1978 [GB] United Kingdom ............... 45815/78
Apr. 25, 1979 [GB] United Kingdom ................ 7914430

[51] Int. Cl.³ .................... A61K 31/12; C07C 49/252
[52] U.S. Cl. .................................. 424/331; 424/341; 568/328; 568/633
[58] Field of Search ............... 568/328, 633; 424/331, 424/341

[56] References Cited

U.S. PATENT DOCUMENTS 3,880,932  4/1975  Anderson ........................... 568/328
3,943,257  3/1976  Anderson et al. .................. 568/328
4,016,779  12/1977 Lake et al. .......................... 424/331

Primary Examiner—James H. Reamer
Attorney, Agent, or Firm—Jacobs & Jacobs

[57] ABSTRACT 4-(6-Methoxy-2-naphthyl)-3-hydroxybutan-2-one and 4-(6-methoxy-2-naphthyl)buta-2,3-diol have good degrees of anti-inflammatory and analgesic activity coupled with an advantageous therapeutic ratio based on gastric irritancy and are non-oestrogenic. Their preparation and use are described.

6 Claims, No Drawings

NAPHTHALENE DERIVATIVES, A PROCESS FOR THEIR PREPARATION AND THEIR USE IN ANTI-INFLAMMATORY PHARMACEUTICAL COMPOSITIONS

CROSS-REFERENCE

This is a continuation of Ser. No. 094,101 filed Nov. 14, 1979, now abandoned.

Belgian Pat. No. 819794 discloses the anti-inflammatory activity of the compounds of the formula (I):

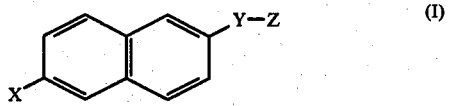

wherein X is a chlorine or bromine atom or a methoxyl, methylthio or alkyl group of 1–4 carbon atoms; Y is a $-CHR_1-CH(R_2)-$, $-CHR_1-CO-$, $-CHR_1-C(OH)R_2-$ or $-C(R_1)=C(R_2)-$ group where $R_1$ and $R_2$ are each a hydrogen atom or a methyl, ethyl group or propyl group and Z is a $R_4$, $(CH_2)_nCOR_4$, $(CH_2)_nCH(OH)R_4$ or $(CH_2)_nC(CH_3)(OH)R_4$ group where $R_4$ is an alkyl group of 1 to 4 carbon atoms and n is 0, 1 or 2; with the proviso that Y–Z contains at least one oxygen atom and not more than one carbonyl group.

It has now been found that certain hitherto unprepared compounds from within the formula (I) have a good degree of anti-inflammatory and analgesic activity coupled with an advantageous therapeutic ratio based on gastric irritancy and are non-oestrogenic.

Accordingly the present invention provides the compounds of the formula (II):

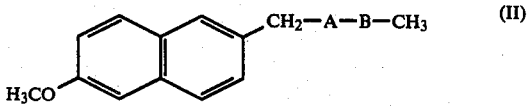

wherein A is a CHOH group and B is a CHOH or CO group.

The compounds of formula (II) have better therapeutic ratios than for example the compound wherein A is CH₂ and B CHOH. The compounds of the formula (II) are more active than the analogous compounds in which A is a CO group. The compounds of the formula (II) are more active than analogous compounds containing a terminal hydroxy group and wherein B is CO. It will therefor be recognised that the present compounds possess particularly advantageous properties for hydroxy compounds within formula (I).

A particularly favoured compound of this invention is 4-(6-methoxy-2-naphthyl)-3-hydroxy-butan-2-one.

A further particularly favoured compound of this invention is 4-(6-methoxy-2-naphthyl)buta-2,3-diol.

The present invention also provides a pharmaceutical composition which comprises a compound of the formula (II) and a pharmaceutically acceptable carrier.

Normally and preferably the compositions of this invention are adapted for administration by mouth. Furthermore, in order to allow exact dose control, the compositions of this invention are provided as unit-dose forms such as capsules, tablets or sachet preparations containing fixed quantities of the composition, for example as a powder or granulate. The unit dose compositions of this invention may contain from 50 mg to 1500 mg of a compound of the formula (II) and will more usually contain from 100 mg to 1000 mg of said compound. Favoured unit dose compositions will contain from 150 mg to 750 mg of a compound of the formula (II), for example about 200, 250, 300, 400, 500 or 600 mgs. The compositions may be administered once or more times a day so that the daily dose for a 70 kg adult will be from 300 mg to 4500 mg and more usually from 500 mg to 3000 mg. Generally 2, 3 or 4 doses are used per day.

The compositions may be formulated in accordance with conventional practice, for example as is known for widely used anti-inflammatory agents such as aspirin, indomethacin, phenylbutazone, ketaprofen, naproxen or the like. Such formulations may contain lubricants, binders, fillers, disintegrants, preservatives, flavourants, colourants or the like. Thus the compositions may contain agents such as magnesium stearate, microcrystalline cellulose, microfine silica, polyvinylpyrrolidone, cross-linked polyvinylpyrrolidone, sodium starch glycollate and the like.

In a process aspect the present invention provides a process for the preparation of a compound of the formula (II) which process comprises either: (a) the reaction of 4-(6-methoxy-2-naphthyl)-2-ethoxy-but-1-ene or 4-(6-methoxy-2-naphthyl)-2-ethoxy-but-2-ene with an organic per acid or (b) the reaction of diazoethane with 6-methoxy-2-naphylacetyl chloride; and thereafter if desired reducing the carbonyl group.

The oxidation may be carried out at a depressed temperature in an organic solvent such as diethyl ether.

The diazetisation reaction may be carried out at a depressed temperature in an organic solvent such as diethyl ether.

The initial crude products may be obtained from the washed ether solution by evaporation of the solvent. This crude product may be purified chromatographically, for example on a silica column using methylene chloride as eluent.

Reduction of the carbonyl group may be effected using sodium borohydride under conventional conditions.

The following Examples are illustrative of the invention:

EXAMPLE 1

4-(6-Methoxy-2-naphthyl)-3-hydroxy-butan-2-one

To a solution of 4-(6-methoxy-2-naphthyl)-2-ethoxy-but-1-ene and 4-(6-methoxy-2-naphthyl)-2-ethoxy-but-2-ene (ratio of about 1:3 respectively) (1.46 g:5.7 m.moles) in diethyl ether (10 ml) and water (1 ml) at 0°–5° C. was added a solution of m-chlorobenzoic acid (1.15 g of 85% pure material:5.7 m.moles) in diethyl ether (10 ml). After stirring rapidly for three minutes the mixture was partitioned between water (50 ml) and ether (100 ml). The aqueous layer was extracted with ether (2×50 ml) and then the combined organic layer was washed with dilute sodium bicarbonate solution (2×50 ml) and water (50 ml) before being dried (Na₂SO₄) and concentrated to afford a white solid (1.6 g). Chromatography of this solid on a silica column (80 g) using methylene chloride as eluent gave 4-(6-methoxy-2-naphthyl)-3-hydroxy-butan-2-one, m.p. 107°–110°, [¹H NMR (CDCl₃) δ7.9–7.0 (m, 6H), 4.55 (broad s, 1H), 4.60–4.35 (dd, 1H), 3.87 (s, 3H), 3.45–2.7 (m, 2H) and 2.16 (s, 3H)] followed by 4-(6-methoxy-2-naphthyl)-1- hydroxy-butan-2-one, m.p. 106°–109°, ['H NMR (CDCl$_3$) δ7.8–7.0 (m, 6H), 4.10 (s, 2H), 3.85 (s, 3H) and 3.25–2.50 (m, 5H, one exchangeable)]

EXAMPLE 2

4-(6-Methoxy-2-naphthyl)buta-2,3-diol

A solution of 3-hydroxy-4-(6-methoxy-2-naphthyl)-butan-2-one (1.22 g:0.005 mole) in isopropanol (100 ml) was treated with sodium borohydride (0.4 g:0.01 mole) and the resulting mixture left stirring overnight. A saturated solution of ammonium chloride (10 ml) was added and the mixture concentrated to remove most of the isopropanol. A further 20 ml of water was added and the resulting white precipitate was collected by filtration and recrystallised from methanol to give 4-(6-methoxy-2-naphthyl)buta-2,3-diol (1.1 g), m.p. 112°–5°.

'HNMR (d$_6$ DMSO) 8.0–7.0 (6H, m) 4.7–4.3 (2H, m) 3.89 (3H, s), 3.8–2.5 (4H, m, two exchangeable), 1.18 (3H, d, J=6 c.p.s.).

Demonstration 1

4-(6-Methoxy-2-naphthyl)-3-hydroxy-butan-2-one (test compound) was examined on a convention carrageenin induced oedema test in rats. Methylcellulose was used as a control. The results obtained were as follows:

|  | Dose (mg/kg/po) | Mean Oedema | Standard Error | Inhib. (%) |
|---|---|---|---|---|
| Control | — | 116 | ±8 | — |
| Test Compound | 45 | 78** | ±9 | 33 |
|  | 15 | 84* | ±8 | 27 |

*p < 0.02
**p < 0.01

4-(6-Methoxy-2-naphthyl)buta-2,3-diol (test compound) was examined as described above. The results obtained were as follows:

|  | Dose (mg/kg/po) | Mean Oedema | Standard Error | Inhib. (%) |
|---|---|---|---|---|
| Control | — | 122 | ±4 | — |
| Test Compound | 45 | 85** | ±8 | 30 |
|  | 15 | 97** | ±7 | 20 |

**p < 0.001

What we claim is:

1. A member selected from the group consisting of 4-(6-methoxy-2-naphthyl)-3-hydroxybutan-2-one and 4-(6-methoxy-2-naphthyl)buta-2,3-diol.

2. A pharmaceutical composition for effecting an analgesic and anti-inflammatory response which comprises an effective amount of a compound according to claim 1 in combination with a pharmaceutically acceptable carrier.

3. A composition according to claim 2 in an orally administrable unit dosage form.

4. A composition according to claim 3 which contains from 150 mg to 750 mg of said compound.

5. 4-(6-Methoxy-2-naphthyl)-3-hydroxy-butan-2-one.

6. 4-(6-Methoxy-2-naphthyl)buta-2,3-diol.

* * * * *